United States Patent

(12) United States Patent
Muller

(10) Patent No.: US 10,449,090 B2
(45) Date of Patent: Oct. 22, 2019

(54) CORNEAL IMPLANT SYSTEMS AND METHODS

(71) Applicant: David Muller, Boston, MA (US)

(72) Inventor: David Muller, Boston, MA (US)

(73) Assignee: Allotex, Inc., Boston, MA (US)

( * ) Notice: Subject to any disclaimer, the term of this patent is extended or adjusted under 35 U.S.C. 154(b) by 546 days.

(21) Appl. No.: 15/055,614

(22) Filed: Feb. 28, 2016

(65) Prior Publication Data

US 2017/0027754 A1 Feb. 2, 2017

Related U.S. Application Data

(60) Provisional application No. 62/199,897, filed on Jul. 31, 2015, provisional application No. 62/239,258, filed on Oct. 8, 2015.

(51) Int. Cl.
*A61F 9/008* (2006.01)
*B23K 26/00* (2014.01)
*B23K 26/361* (2014.01)
*B23K 26/12* (2014.01)
*B23K 26/38* (2014.01)
(Continued)

(52) U.S. Cl.
CPC ........ *A61F 9/00804* (2013.01); *A61F 9/0081* (2013.01); *A61F 9/00812* (2013.01);
(Continued)

(58) Field of Classification Search
None
See application file for complete search history.

(56) References Cited

U.S. PATENT DOCUMENTS 2,302,918 A    11/1942   Smith
4,646,720 A    3/1987   Peyman et al.
(Continued)

FOREIGN PATENT DOCUMENTS

CA    2650883    11/2007
EP    2371329 A1    10/2011
(Continued)

OTHER PUBLICATIONS

International Search Report for corresponding PCT International Patent Application No. PCT/US2016/021539, dated Jul. 7, 2016 (2 pages).
(Continued)

*Primary Examiner* — Mathieu D Vargot
(74) *Attorney, Agent, or Firm* — McDonnell Boehnen Hulbert & Berghoff LLP

(57) ABSTRACT

A system for forming a corneal implant includes a cutting apparatus, which includes a laser source that emits a laser and optical elements that direct the laser. The system includes a controller implemented with at least one processor and at least one data storage device. The controller generates a sculpting plan for modifying a first shape of a lenticule formed from corneal tissue and achieving a second shape for the lenticule to produce a corneal implant with a refractive profile to reshape a recipient eye. The sculpting plan is determined from measurements relating to the lenticule having the first shape and information relating to a refractive profile for a corneal implant. The controller controls the cutting apparatus to direct, via the one or more optical elements, the laser from the laser source to sculpt the lenticule according to the sculpting plan to produce the corneal implant with the refractive profile.

16 Claims, 11 Drawing Sheets

(51) Int. Cl.
  *B23K 26/402* (2014.01)
  *A61F 2/14* (2006.01)
  *B23K 103/00* (2006.01)

(52) U.S. Cl.
  CPC ...... *A61F 9/00831* (2013.01); *A61F 9/00834* (2013.01); *B23K 26/127* (2013.01); *B23K 26/361* (2015.10); *B23K 26/38* (2013.01); *B23K 26/402* (2013.01); *A61F 2/145* (2013.01); *A61F 2009/00842* (2013.01); *A61F 2009/00851* (2013.01); *A61F 2009/00872* (2013.01); *A61F 2009/00878* (2013.01); *A61F 2009/00893* (2013.01); *A61F 2009/00895* (2013.01); *B23K 2103/32* (2018.08)

(56) References Cited

U.S. PATENT DOCUMENTS

| | | | |
|---|---|---|---|
| 4,764,930 A | 8/1988 | Bille et al. | |
| 4,793,344 A | 12/1988 | Cumming et al. | |
| 5,312,428 A | 5/1994 | Lieberman | |
| 5,336,261 A | 8/1994 | Barrett et al. | |
| 5,549,632 A | 8/1996 | Lai | |
| 5,552,452 A | 9/1996 | Khadem et al. | |
| 5,647,865 A * | 7/1997 | Swinger | A61F 9/008 128/898 |
| 5,702,414 A | 12/1997 | Richter et al. | |
| 5,919,185 A | 7/1999 | Peyman | |
| 5,993,438 A | 11/1999 | Juhasz et al. | |
| 6,030,398 A | 2/2000 | Klopotek | |
| 6,063,073 A | 5/2000 | Peyman | |
| 6,099,541 A | 8/2000 | Klopotek | |
| 6,197,019 B1 | 3/2001 | Peyman | |
| 6,210,401 B1 | 4/2001 | Lai | |
| 6,254,595 B1 | 7/2001 | Juhasz et al. | |
| 6,280,470 B1 | 8/2001 | Peyman | |
| 6,325,792 B1 | 12/2001 | Swinger et al. | |
| RE37,585 E | 3/2002 | Mourou et al. | |
| 6,436,092 B1 | 8/2002 | Peyman | |
| 6,544,286 B1 | 4/2003 | Perez | |
| 6,702,807 B2 | 3/2004 | Peyman | |
| 6,949,093 B1 | 9/2005 | Peyman | |
| 7,044,602 B2 | 5/2006 | Chernyak | |
| 7,497,866 B2 | 3/2009 | Perez | |
| 7,585,075 B2 | 9/2009 | Marmo | |
| 7,611,507 B2 | 11/2009 | Raksi et al. | |
| 7,776,086 B2 | 8/2010 | Miller | |
| 7,828,844 B2 | 11/2010 | Marmo et al. | |
| 7,883,520 B2 | 2/2011 | Gaeckle et al. | |
| 7,973,079 B2 | 7/2011 | Mata et al. | |
| 7,992,906 B2 | 8/2011 | Nigam | |
| 8,057,541 B2 | 11/2011 | Dishler et al. | |
| 8,092,490 B2 | 1/2012 | Redmond et al. | |
| 8,162,953 B2 | 4/2012 | Dishler et al. | |
| 8,240,850 B2 | 8/2012 | Apter et al. | |
| 8,246,609 B2 * | 8/2012 | Zickler | A61F 9/00804 128/898 |
| 8,469,948 B2 | 6/2013 | Dishler et al. | |
| 8,540,727 B2 | 9/2013 | Dishler et al. | |
| 8,668,735 B2 | 3/2014 | Nigam et al. | |
| 8,753,321 B2 | 6/2014 | Mrochen et al. | |
| 8,784,406 B2 | 7/2014 | Rathjen | |
| 8,845,624 B2 | 9/2014 | Raksi et al. | |
| 8,900,296 B2 | 12/2014 | Holliday et al. | |
| 8,949,093 B2 | 2/2015 | Degani et al. | |
| 9,005,280 B2 | 4/2015 | Nigam | |
| 9,271,828 B2 | 3/2016 | Schneider et al. | |
| 9,345,569 B2 | 5/2016 | Plambeck et al. | |
| 2001/0018612 A1 | 8/2001 | Carson et al. | |
| 2003/0014042 A1 | 1/2003 | Juhasz et al. | |
| 2003/0153904 A1 | 8/2003 | Patel | |
| 2004/0243111 A1 | 12/2004 | Bendett et al. | |
| 2005/0080484 A1 | 4/2005 | Marmo et al. | |
| 2005/0125001 A1 | 6/2005 | Danon | |
| 2006/0020259 A1 | 1/2006 | Baumeister et al. | |
| 2006/0100612 A1 | 5/2006 | van der Heyd et al. | |
| 2006/0116762 A1 | 6/2006 | Hong et al. | |
| 2006/0134170 A1 | 6/2006 | Griffith et al. | |
| 2006/0192921 A1 | 8/2006 | Loesel et al. | |
| 2006/0276888 A1 | 12/2006 | Lee et al. | |
| 2007/0129797 A1 | 6/2007 | Lang et al. | |
| 2007/0203577 A1 | 8/2007 | Dishler et al. | |
| 2007/0208325 A1 | 9/2007 | Kurtz | |
| 2007/0208422 A1 | 9/2007 | Walter et al. | |
| 2007/0255401 A1 | 11/2007 | Lang | |
| 2008/0033408 A1 | 2/2008 | Bueler et al. | |
| 2008/0082086 A1 | 4/2008 | Kurtz et al. | |
| 2008/0262610 A1 | 10/2008 | Lang et al. | |
| 2008/0306573 A1 | 12/2008 | Campin et al. | |
| 2009/0018532 A1 | 1/2009 | Salin | |
| 2009/0051876 A1 | 2/2009 | Seiler et al. | |
| 2009/0118718 A1 | 5/2009 | Raksi et al. | |
| 2010/0211051 A1 | 8/2010 | Weston et al. | |
| 2010/0241224 A1 | 9/2010 | Lai et al. | |
| 2010/0298443 A1 | 11/2010 | Widder et al. | |
| 2011/0029073 A1 | 2/2011 | Liang | |
| 2011/0290681 A1 | 12/2011 | Nigam | |
| 2011/0294891 A1 | 12/2011 | Widder et al. | |
| 2012/0108665 A1 | 5/2012 | Mata et al. | |
| 2012/0202885 A1 | 8/2012 | Widder et al. | |
| 2012/0203238 A1 | 8/2012 | Nigam | |
| 2012/0288568 A1 | 11/2012 | Widder et al. | |
| 2012/0309835 A1 | 12/2012 | Widder et al. | |
| 2013/0041354 A1 | 2/2013 | Brownell et al. | |
| 2013/0238091 A1 | 9/2013 | Danta et al. | |
| 2014/0128821 A1 | 5/2014 | Gooding et al. | |
| 2014/0142200 A1 | 5/2014 | Duan et al. | |
| 2014/0200665 A1 | 7/2014 | Lang et al. | |
| 2014/0232988 A1 | 8/2014 | Kersting et al. | |
| 2014/0264980 A1 | 9/2014 | Muller | |
| 2014/0276677 A1 | 9/2014 | Brownell et al. | |
| 2015/0080865 A1 | 3/2015 | Holliday et al. | |
| 2015/0126970 A1 | 5/2015 | Thompson | |
| 2015/0133901 A1 | 5/2015 | Serdarevic et al. | |
| 2015/0168250 A1 | 6/2015 | Saxer et al. | |
| 2015/0182331 A1 | 7/2015 | Blum et al. | |
| 2015/0238308 A1 | 8/2015 | Ishak et al. | |
| 2015/0250652 A1 | 9/2015 | Holliday et al. | |
| 2015/0277145 A1 | 10/2015 | Bakaraju et al. | |
| 2015/0366657 A1 | 12/2015 | Sharma | |
| 2016/0022493 A1 | 1/2016 | Peyman | |
| 2016/0062145 A1 | 3/2016 | Brennan et al. | |
| 2016/0170232 A1 | 6/2016 | Wildsmith | |
| 2016/0184085 A1 | 6/2016 | Schneider et al. | |
| 2017/0115509 A1 | 4/2017 | Brennan et al. | |

FOREIGN PATENT DOCUMENTS

| | | |
|---|---|---|
| RU | 2203006 C1 | 4/2003 |
| RU | 2470616 C1 | 12/2012 |
| WO | WO 93/08878 | 5/1993 |
| WO | WO 94/09849 | 5/1994 |
| WO | WO 03/075778 | 9/2003 |
| WO | WO 2004/028357 | 4/2004 |
| WO | WO 2006/011011 | 2/2006 |
| WO | WO 1007/143111 | 12/2007 |
| WO | WO 2008/030699 | 3/2008 |
| WO | WO 2008/060810 | 5/2008 |
| WO | WO 2008/131888 | 11/2008 |
| WO | WO 2009/146151 | 12/2009 |
| WO | 2011152861 A2 | 12/2011 |
| WO | WO 2012/035403 | 3/2012 |
| WO | WO 2013/170966 | 12/2012 |
| WO | 2013159798 A1 | 10/2013 |
| WO | WO 2015/003779 | 1/2015 |
| WO | WO 2015/183941 | 12/2015 |

OTHER PUBLICATIONS

Written Opinion of the International Searching Authority for corresponding PCT International Patent Application No. PCT/US2016/021539, dated Jul. 7, 2016 (4 pages).

(56) References Cited

OTHER PUBLICATIONS

Hara et al., Xenotransplantation—The Future of Corneal Transplantation?.
Miclea et al., Applanation-Free Femtosecond Laser Processing of the Cornea.
Moore et al., Fate of Lyophilized Xenogeneic Corneal Lenticules in Intrastromal Implantation and Epikeratophakia.
Shaw, Eyelid Pressure on the Cornea, p. 107-143.
Smith et al., Effect of Defocus on on-axis Wave Aberration of a Centered Optical System.
Studer et al., Biomechanical Modeling of Femtosecond Laser Keyhole Endokeratophakia Surgery.
Whitford et al., Biomechanical Model of the Human Corena: Considering Shear Stiffness and Regional Variation of Dollagen Anisotropy and Density.

\* cited by examiner

CORNEAL IMPLANT SYSTEMS AND METHODS

CROSS-REFERENCE TO RELATED APPLICATIONS

This application claims the benefit of, and priority to, U.S. Provisional Patent Application Ser. No. 62/199,897, filed Jul. 31, 2015, and U.S. Provisional Patent Application Ser. No. 62/239,258, filed Oct. 8, 2015, the contents of these applications being incorporated entirely herein by reference.

FIELD OF THE INVENTION

The present disclosure relates generally to systems and methods for correcting vision, and more particularly, to systems and methods that employ implants to reshape the cornea in order to correct vision.

BACKGROUND

A variety of eye disorders, such as myopia, hyperopia, astigmatism, and presbyopia, involve abnormal shaping of the cornea. This abnormal shaping prevents the cornea from properly focusing light onto the retina in the back of the eye (i.e., refractive error). A number of treatments attempt to reshape the cornea so that the light is properly focused. For instance, a common type of corrective treatment is LASIK (laser-assisted in situ keratomileusis), which employs a laser to reshape the cornea surgically.

SUMMARY

According to aspects of the present disclosure, embodiments employ implants to reshape the cornea in order to correct vision. For instance, such embodiments may address the refractive errors associated with eye disorders such as myopia, hyperopia, astigmatism, and presbyopia. The implants may be formed from natural tissue, such as donor corneal tissue.

An example system for forming a corneal implant includes a cutting apparatus. The cutting apparatus includes a laser source that emits a laser and one or more optical elements that direct the laser from the laser source. The system includes a controller implemented with at least one processor and at least one data storage device. The controller is configured to generate a sculpting plan for modifying a first shape of a lenticule formed from corneal tissue and achieving a second shape for the lenticule to produce a corneal implant with a refractive profile to reshape a recipient eye. The sculpting plan is determined from measurements relating to the lenticule having the first shape and information relating to a refractive profile for a corneal implant. The controller is configured to control the cutting apparatus to direct, via the one or more optical elements, the laser from the laser source to sculpt the lenticule according to the sculpting plan to produce the corneal implant with the refractive profile.

Another example system for forming a corneal implant includes a receptacle configured to receive a lenticule formed from corneal tissue and to maintain a state of the lenticule. The system includes a cutting apparatus. The cutting apparatus includes a laser source that emits a laser and one or more optical elements that direct the laser from the laser source to the receptacle to cut the lenticule. The receptacle is configured to allow the laser to cut the lenticule while the lenticule is disposed in the receptacle.

Yet another system for implanting a corneal implant includes a cutting apparatus. The cutting apparatus includes a laser source that emits a laser and one or more optical elements that direct the laser from the laser source. The system includes a controller implemented with at least one processor and at least one data storage device. The controller is configured to determine one or more holes to be formed in the Bowman's membrane of a recipient eye. The one or more holes allow at least keratocytes and glycosaminoglycans to migrate from the stroma of the recipient eye to a corneal implant implanted between the Bowman's membrane and the epithelium. The corneal implant is formed from corneal tissue. The controller is configured to control the cutting apparatus to form the one or more holes in the Bowman's membrane.

An example method for forming a corneal implant includes receiving a corneal tissue. The method includes identifying a plurality of sections of the corneal tissue having different respective structural characteristics. The method includes determining measurements relating to at least one of the sections according to the respective structural characteristics. The method includes separating, with a cutting apparatus, the at least one section from the corneal tissue according to the measurements.

Figure 1A:
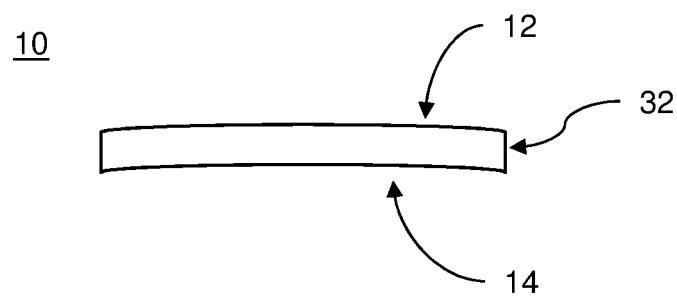
FIG. 1A illustrates a view of an example implant formed from natural tissue according to aspects of the present disclosure.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DESCRIPTION

Example systems and methods employ implants to reshape the cornea in order to correct vision. For instance, such embodiments may address the refractive errors associated with eye disorders such as myopia, hyperopia, astigmatism, and presbyopia.

Example systems and methods employ implants that are formed from natural tissue. In particular, the implants may be formed from donor corneal tissue. For instance, the implants may be formed as allografts, i.e., tissue that is transplanted between members of the same species. Alternatively, the implants may be formed as xenografts, i.e., tissue that is transplanted between members of different species.

The methods and implants of the present disclosure exhibit significant improvements over prior attempts to correct vision utilizing implants. For example, some prior attempts to correct vision utilized implants made from synthetic materials; however, such implants made from synthetic materials did not work well for a variety of reasons (e.g., the irregularity of the collagen matrix of an eye, differences in the state of hydration of the synthetic material and the collagen matrix of an eye, lack of biocompatibility, etc.). The methods and implants of the present disclosure, which are made from natural tissue, overcome the deficiencies of such prior attempts. In particular, for example, the methods and implants of the present disclosure, which are made from natural tissue, exhibit greater biocompatibility with a patient's cornea, more closely match the index of refraction of the patient's cornea, can be maintained at a state of hydration that is required for implantation (e.g., a state of hydration that is similar to that of the implantation site), and ensures that sufficient gas and nutrients can be exchanged within the patient's cornea. Such advantages have not been achieved or successfully commercialized, at least in part, due to a lack of suitable methods and systems for manufacturing implants made from natural tissue.

Figure 1B:
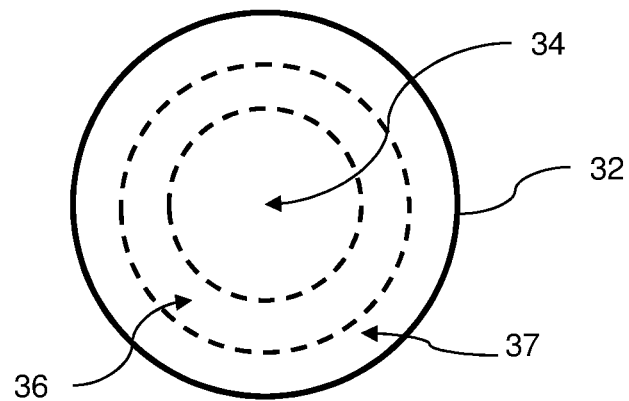
FIG. 1B illustrates another view of the example implant of FIG. 1A.

FIGS. 1A and 1B illustrate an example implant 10 according to aspects of the present disclosure. The implant 10 is formed from natural tissue or, more particularly, for example, a donor cornea. As shown in FIG. 1A, the implant 10 has a front (anterior) surface 12 corresponding to the anterior of the eye when implanted and a back (posterior) surface 14 corresponding to the posterior of the eye when implanted. While the example implant 10 illustrated in FIG. 1 has a front surface 12 and back surface 14 that form a meniscus shape, the implant 10 may have a plano-convex shape, a plano-concave shape, a bi-convex shape, or the like. Additionally, the front surface 12 and/or the back surface 14 may be spherical and/or aspherical.

To facilitate description of some aspects of the implant 10, FIG. 1B shows a top plan view of the implant 10 having a central region 34, a mid-peripheral region, 36, an outer peripheral region 37, and a peripheral edge 32. It should be understood that such regions 34, 36, 37 are intended as one non-limiting example and the implants 10 may have any number (i.e., one or more) of regions of any size. Additionally, while the example implant 10 illustrated in FIGS. 1A and 1B has a circular perimeter shape defined by the peripheral edge 32, the implant 10 may have an oval shape, a polygonal shape, a non-polygonal shape, or the like.

According to aspects of the present disclosure, the back surface 14 of the implant 10 may be shaped to have a surface profile that generally corresponds to a surface profile of an implantation site of a patient's cornea, and the front surface 12 of the implant 10 may be shaped to have a surface profile that provides a predetermined refractive correction. To achieve this, the implant 10 may be precisely formed according to conditions specific to the patient receiving the implant 10.

Figure 2:
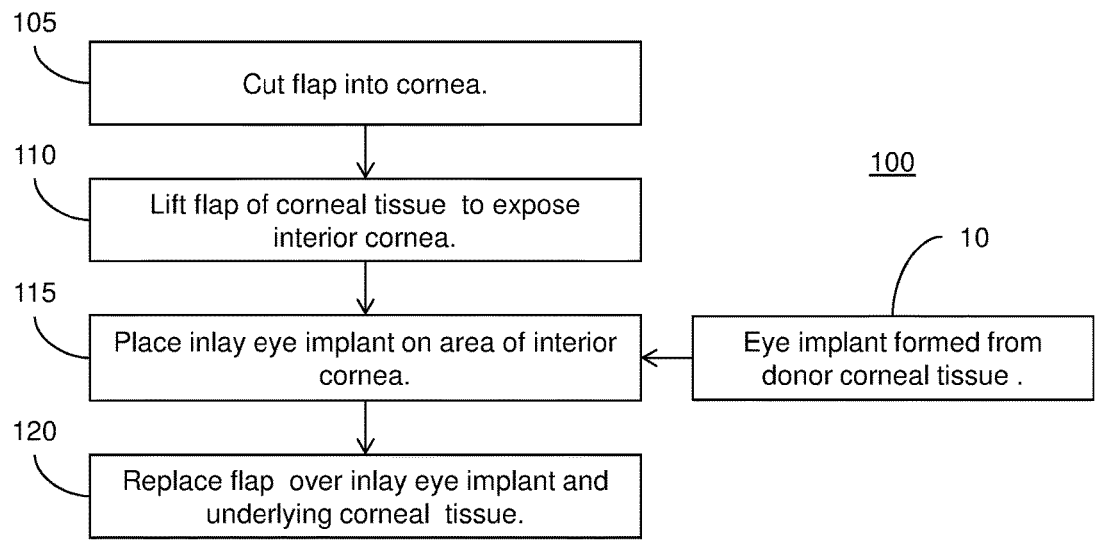
FIG. 2 illustrates an example procedure employing an inlay implant formed from natural tissue, according to aspects of the present disclosure.

FIG. 2 illustrates an example procedure 100 for implantation of the implant 10 according to aspects of the present disclosure. In step 105, a flap is formed in a cornea 16. For example, a laser (e.g., a femtosecond laser), a mechanical keratome, other cutting mechanisms (e.g., a blade), etc., may be used to cut the flap. In some embodiments, the flap may be as thin as flaps that are cut for Sub-Bowman's Keratomileusis. The flap is sufficiently large to provide stability and ease of handling. In step 110, the flap of corneal tissue is lifted to expose the corneal interior 18. Thus, as a result of step 105 and step 110, an anterior portion 20 of the cornea 16 is separated from a posterior portion 22 of the cornea 16 to expose a stromal bed 24 upon which the implant 10 can be implanted.

In step 115, the implant 10 formed from donor corneal tissue is placed onto the stromal bed 24 at an implantation site in the exposed interior area 18 of the cornea 16 formed in step 105. The back surface 14 of the implant 10 is placed into contact with the bed 24 and may have a shape that corresponds to the shape of the bed 24 at the implantation site. In some cases, the back surface 14 of the implant 10 may have a non-flat surface curvature that generally corresponds to the non-flat curvature of the bed 24 at the implantation site. Alternatively, the back surface 14 of the implant 10 may be generally flat to correspond with a generally flat bed 24 at the implantation site.

According to some aspects, the implant 10 is implanted into the cornea 16 in a hydrated state. In some cases, the implant 10 may be transferred, via an insertion device (not shown), from a storage media containing the implant 10 prior to the procedure 100 to the implantation site. In other cases, the implant 10 may be transferred from a controlled environment directly and immediately to the implantation site. For example, the insertion device may be configured to maintain the implant 10 in the desired hydrated state. In step 120, the flap is replaced over the implant 10 and corneal interior 18. With the flap in place after step 120, the cornea 16 heals and seals the flap of corneal tissue to the rest of the cornea 16 (i.e., the anterior portion 20 seals to the posterior portion 22 to enclose the implant 10).

Figure 3:
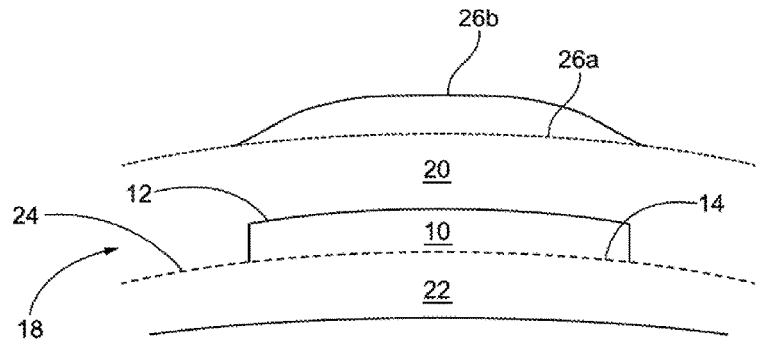
FIG. 3 illustrates an inlay implanted within corneal tissue, according to aspects of the present disclosure.

As shown in FIG. 3, after the procedure 100, the implant 10 is surgically inserted within the interior 18 of the cornea 16 with an anterior portion 20 of corneal tissue 16 disposed over the implant 10. Accordingly, in FIGS. 2-3, the implant 10 is implanted as an inlay implant because it is surgically implanted within the interior 18 of the cornea 16 (i.e., between the anterior portion 20 and a posterior portion 22 of the cornea 16). The implant 10 changes the shape of the cornea 16 as evidenced by a change in the anterior corneal surface 26a, 26b (e.g., in FIG. 3, the anterior corneal surface is shown as a dashed line 26a prior to the implantation and as a solid line 26b after implantation). This change in shape of the anterior corneal surface 26a, 26b results in corrective modification of the cornea 16, e.g., refractive correction. For example, the implant 10 may address the loss of near vision associated with presbyopia. To correct the effects of presbyopia, for instance, the implant 10 may be sized and positioned so that the change to the corneal shape improves near vision while having minimal effect on distance vision, which requires no correction. In general, however, the implants 10 may have any size or shape to produce the necessary desired correction. For instance, in some cases, the implant 10 may have a diameter of up to approximately 10 mm, but preferably not more than approximately 7 mm.

While the implant 10 shown in FIG. 3 is employed as an inlay implant 10, it is understood that applying the implant 10 to the cornea 16 is not limited to the procedure 100 described above and that other procedures may be employed. For example, rather than forming a flap, a pocket having side walls with an opening may be formed (e.g., with a femtosecond laser or other cutting mechanism) to receive the implant 10. Stated more generally, the cornea 16 can be cut to separate the anterior portion 20 of the cornea 16 (e.g., the flap or an anterior section of a pocket) from the posterior portion 22 of the cornea 16, exposing the corneal interior 18 upon which the implant 10 can then be placed at an implantation site and subsequently covered by the anterior portion 20 of the cornea 16.

Figure 4A:
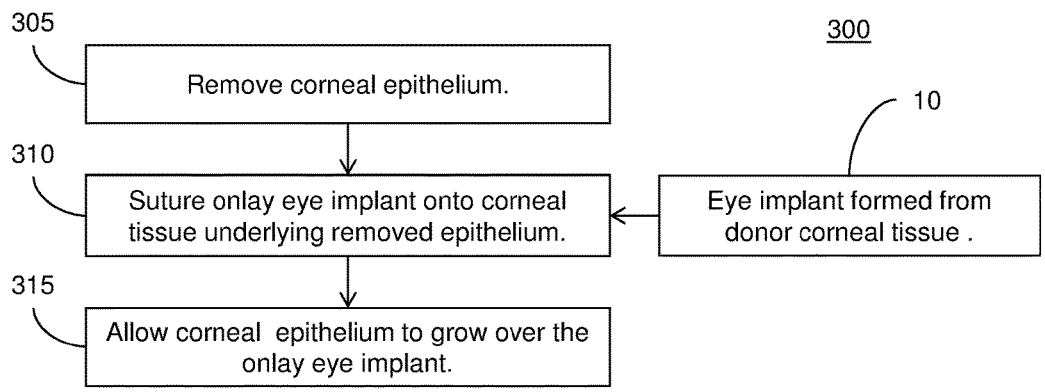
FIG. 4A illustrates an example procedure employing an onlay implant formed from natural tissue, according to aspects of the present disclosure.

In other embodiments, the implant 10 may be employed as an onlay implant, where it is placed on an outer portion 28 of the cornea 16 just under the epithelium 30 so that the epithelium 30 can grow over the implant 10. For instance, in an example procedure 300 shown in FIG. 4A, at least a portion of the epithelium 30 is removed (e.g., scraped) from the cornea 16 in step 305 and the implant 10 is sutured over the outer portion 28 of the corneal tissue 16 in step 310 where the epithelium 30 is allowed to grow over the implant 10 in step 315.

Figure 4B:
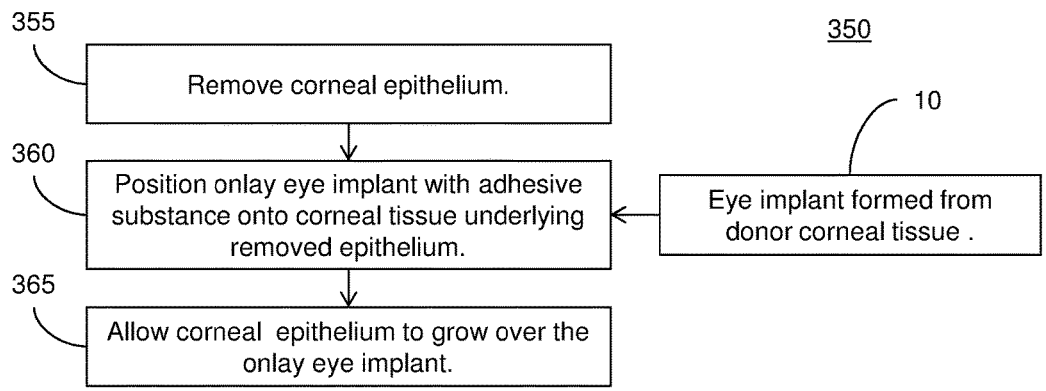
FIG. 4B illustrates another example procedure employing an onlay implant formed from natural tissue, according to aspects of the present disclosure.

Alternatively, in another example procedure 350 shown in FIG. 4B, at least a portion of the epithelium 30 is removed (e.g., scraped) from the cornea in step 355 and the implant 10 is stably positioned with an adhesive substance over the outer portion 28 of the corneal tissue 16 in step 360 where the epithelium 30 is allowed to grow over the implant 10 in step 365. The adhesive substance, for example, may be a synthetic, biocompatible hydrogel that creates a temporary, soft, and lubricious surface barrier over the implant 10, keeping the implant 10 in place for the growth of the epithelium 30. According to some aspects of the present disclosure, the adhesive substance can include a cross-linking agent, as will be described in further detail below. In one non-limiting example, the onlay implant 10 can be dipped into riboflavin to facilitate assist in visualizing placement of the implant 10 on the outer portion 28 of the cornea 16. After placement onto the outer portion 28, the cross-linking agent can be activated (e.g., via a photoactivating light) to hold the implant 10 to the outer portion 28 of the cornea 16.

Figure 5:
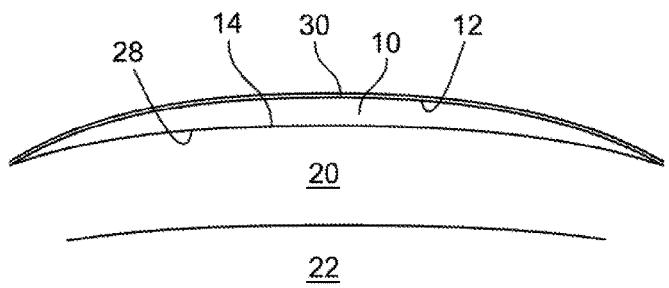
FIG. 5 illustrates an onlay implanted under a corneal epithelium, according to aspects of the present disclosure.

Like the inlay implant, the onlay implant changes the shape of the cornea 16 and results in corrective modification of the cornea 16. Thus, the onlay implant may be applied to treat all refractive errors. As shown in FIG. 5, the corneal epithelium 30 grows over the onlay implant 10 which is implanted on the outer portion 28 of the corneal tissue 16. The epithelium 30 is generally about 50 micrometers (i.e., 5-6 cell layers) thick and generally regenerates when the cornea 16 is damaged or partially removed. To facilitate recovery after implantation, the shape of the implant 10 is configured to facilitate the advancement of the epithelium 30 smoothly over the implant 10 during regeneration. More particularly, the implant 10 can have a tapered profile at the outer peripheral region 37 such that the implant 10 becomes thinner from the mid-periphery region 36 towards the peripheral edge 32 of the implant 10. Formed from donor corneal tissue, the implant 10 advantageously promotes effective growth of the epithelium 30. In addition, the implant 10 provides the accuracy required to achieve the desired correction.

As described above, the onlay implant 10 is implanted on an outer portion 28 of the cornea 16 under the corneal epithelium 30. The Bowman's membrane is a smooth, acellular, nonregenerating layer, located between the epithelium and the stroma in the cornea of the eye. It is the outermost layer just below the epithelium. According to some aspects, the onlay implant 10 may be implanted between the Bowman's membrane and the epithelium 30. According to additional and/or alternative aspects, the onlay implant 10 may be implanted between one or more cell layers of the epithelium 30. According to still other additional and/or alternative aspects, the onlay implant 10 may be implanted such that a minor portion penetrates the Bowman's membrane and/or the stroma so long as a major portion of the onlay implant 10 is located on or above the Bowman's membrane and under the outermost layer of the epithelium 30.

According to one approach, a slight relief (e.g., cavity) is formed in the Bowman's layer to facilitate positioning of the onlay implant 10 and to help keep the onlay implant 10 in position during healing. This approach can be employed to lower the edges of the onlay implant 10, so that epithelial under growth is prevented and the epithelium 30 can grow more easily over the onlay implant 10.

Keratocytes are specialized fibroblasts that reside in the stroma and play a major role in maintaining clarity of corneal collagen, healing corneal wounds, and synthesizing corneal components. Meanwhile, glycosaminoglycans (GAGs) help keep corneal tissue hydrated and prevent corneal haze. In general, keratocytes and GAGs help maintain the health of corneal tissue. As described above, the onlay implant 10 in some implementations is disposed above the Bowman's membrane. Due to the structure of the Bowman's membrane, keratocytes, GAGs, and other cells/substances cannot migrate from the stroma and through the Bowman's membrane to the onlay implant 10. In some cases, the onlay implant 10 may be sufficiently thin to obviate any need for keratocytes, GAGs, and other cells/substances to remain healthy. In other cases, however, various approaches may be employed to allow migration of keratocytes, GAGs, and other cells/substances to the onlay implant 10. (Although contemplated, complete removal of the Bowman's membrane may not be feasible as the Bowman's membrane provides structural strength to the eye.)

Figure 4C:
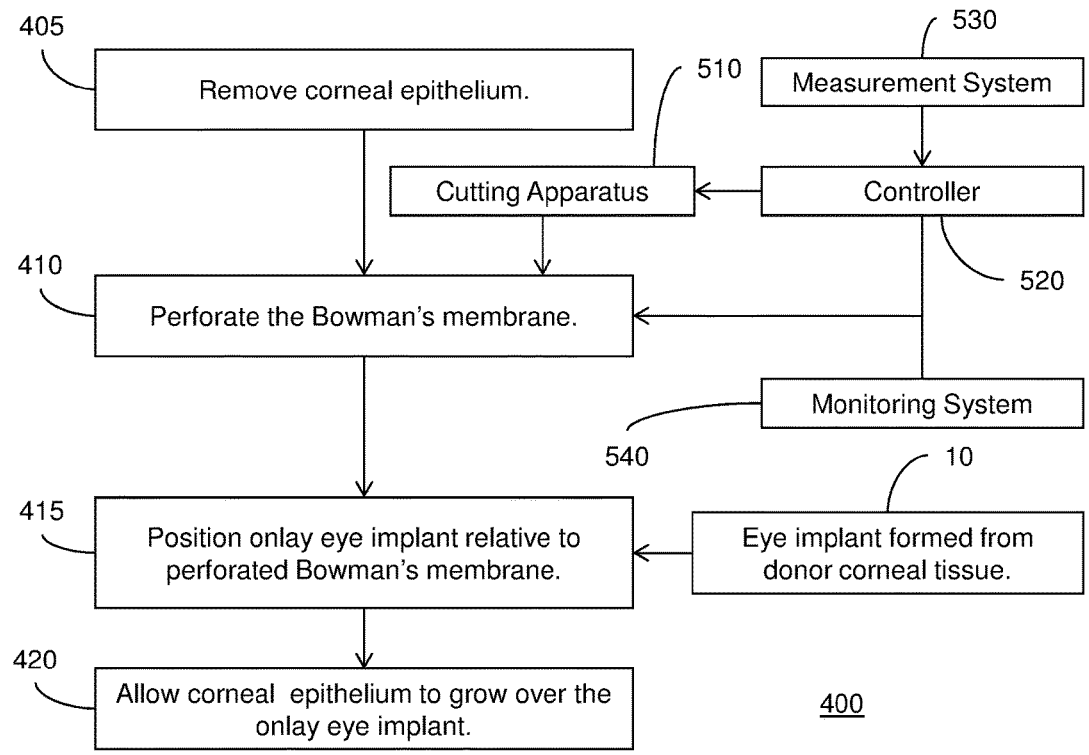
FIG. 4C illustrates yet another example procedure employing an onlay implant formed from natural tissue where one or more holes are formed in the Bowman's membrane, according to aspects of the present disclosure.

According to an example procedure 400 illustrated in FIG. 4C, the Bowman's membrane is perforated to provide passages from the stroma to the onlay implant 10. In other words, one or more holes are formed through the Bowman's membrane so that keratocytes, GAGs, and other cells/substances can migrate to the onlay implant 10 above the Bowman's membrane. The example procedure 400 includes removing (e.g., scraping) at least a portion of the epithelium 30 from the cornea in step 405, perforating the Bowman's membrane in step 410, and positioning the onlay implant 10 relative (e.g., over) the perforated Bowman's membrane in step 415 where the epithelium 30 is allowed to grow over the onlay implant 10 in step 420.

For a relatively small onlay implant 10, a single hole that corresponds to the size and shape of the small onlay implant can be formed through the Bowman's membrane and the small onlay implant can be positioned in the hole. For example, a circular hole with a diameter of approximately 2 mm may be formed in the Bowman's membrane to accommodate a circular onlay implant with a diameter of approximately 2 mm.

As illustrated in FIG. 4C, perforations in the Bowman's membrane may be formed with a cutting apparatus 510. The cutting apparatus 510 may include a laser source that emits a laser, such as an excimer laser or a femtosecond laser, capable of cutting the Bowman's membrane. The cutting apparatus 510 may also include one or more optical elements that direct the laser from the laser source. Such optical elements may include any combination of lenses, mirrors, filters, beam splitters, etc. In some embodiments, the formation of the holes in the Bowman's membrane with the cutting apparatus 510 may be guided by a mask that is placed over the Bowman's membrane and allows the laser to penetrate Bowman's membrane at specific predetermined positions.

Furthermore, a controller 520 may be employed to determine the number, size, and position of one or more holes that optimize flow through the Bowman's membrane and minimize biomechanical instability caused by the holes. The controller may also determine the one or more holes according at least to a size of the corneal implant.

The controller 520 may employ a measurement system 530 that provides information about structural aspects of the eye, including the Bowman's membrane. Additionally, a monitoring system 540 may be employed to monitor the proper formation of the holes. The controller 510 may also control aspects of the cutting apparatus 510.

According to some aspects of the present disclosure, the implant 10 (i.e., as an inlay or as an onlay) can be shaped to accommodate a single zone of power for vision correction. As a non-limiting example, the implant 10 can be shaped primarily to accommodate near-vision. As another non-limiting example, the implant 10 can be shaped to accommodate mid-vision or far-vision. According to other aspects of the present disclosure, the implant 10 can be shaped to provide multi-focality, e.g., accommodate more than one zone of different power. For example, the implant 10 can include a plurality of different portions that are each shaped to accommodate a different zone of power. While the implant 10 illustrated in FIG. 1 is described as having a central region 34, a mid-peripheral region 36, and an outer peripheral region 37, it should be understood that the implant 10 can have any other number of regions, each having a different power. As one non-limiting example, the central region 34 of the implant 10 may be shaped to accommodate near-vision, the mid-peripheral region 36 of the implant 10 may be shaped to accommodate mid-vision, and/or the outer peripheral region 37 of the implant 10 may be shaped to accommodate far-vision.

Figure 6:
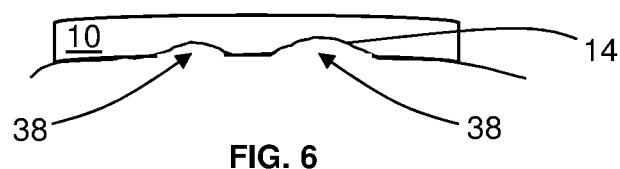
FIG. 6 illustrates an example implant for addressing surface irregularities, according to aspects of the present disclosure.
Figure 7A:
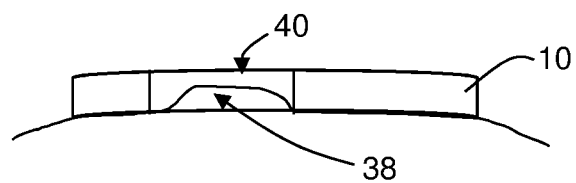
FIG. 7A illustrates a view of another example implant for addressing surface irregularities, according to aspects of the present disclosure.
Figure 7B:
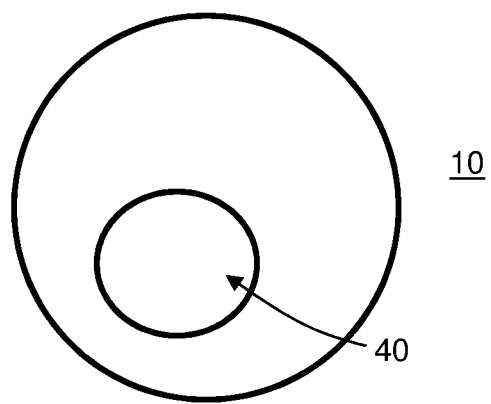
FIG. 7B illustrates another view of the example implant of FIG. 7A.

In some cases, patients with ectasia or keratoconus, for example, have corneal surface irregularities. Because their corneas 16 are typically thinner than normal, ablation techniques cannot be employed to smooth the shape of the corneas 16 to a more regular shape. To address this problem, a custom implant 10 (i.e., an inlay or an onlay) may be formed to have a shape that is generally the inverse of the surface irregularity and thus compensates for the surface irregularity. The implant 10 may be formed to have a front surface 12 that generally reproduces the back surface 14 curvature. For example, the implant 10 may be relatively thinner over areas of the cornea 16 that are relatively higher (i.e., extend outwardly), and vice versa. A non-limiting example of an onlay implant 10 that having a back surface 14 that is the inverse of the surface irregularities 38 of the outer portion 28 of the cornea 16 is illustrated in FIG. 6. The implant 10 may even have an aperture 40 that is positioned over steep and high portions of the cornea 16. For example, FIGS. 7A-7B illustrate a non-limiting example of an onlay implant 10 having an aperture 40 over a steep and high portion 42 of the outer portion 28 of the cornea 16. The implant 10 may be implanted as an inlay or an onlay according to the techniques described above.

It should be understood that the procedures 100 and 200 described above can include additional steps and/or the steps can be modified. For example, according to some aspects of the present disclosure, one or more cross-linking agents may be applied to the implants 10 to strengthen or stiffen them before they are implanted. In other embodiments, one or more cross-linking agents may be employed to stabilize the patient's cornea 16 after the implants 10 are implanted. In yet further embodiments, the cross-linking agents may be employed as an adhesive substance to hold the implant 10 stably in place for the implant procedures. For example, in the example procedure 350 above, an onlay implant 10 may be dipped into a cross-linking agent and the onlay implant 10 is held stably in place for subsequent growth of the epithelium 30 by the cross-linking that occurs with surrounding corneal tissue 16. In some cases, the application of cross-linking agent allows the implant 10 to be more easily visualized for the implant procedure.

The cross-linking agents that may be employed according to aspects of the present disclosure include, but are not limited to, Riboflavin, Rose Bengal, or Glutaraldehyde. For example, a dose of Ribloflavin may be applied topically and photoactivating light, such as ultraviolet (UV) light, may be applied to the Riboflavin to initiate cross-linking. Similarly, a dose of Rose Bengal may be applied topically and photoactivating light, such as visible, e.g., green, light, may be applied to the Rose Bengal to initiate cross-linking. The photoactivating light initiates cross-linking activity by causing the applied Riboflavin or Rose Bengal to release reactive radicals, such as singlet oxygen, in the corneal tissue. It is understood however, that aspects of the present disclosure do not require the application of a cross-linking agent.

The implants can be precisely manufactured according to patient specific conditions. For instance, the implants of the present disclosure can be manufactured to have a shape that generally corresponds to a shape of an implantation site of the patient's cornea, provides a predetermined amount of refractive correction, and/or addresses corneal irregularities. Approaches for producing implants from donor corneal tissue are described, for instance, in U.S. Patent Application Publication No. 2014/0264980, filed Jan. 10, 2014 and titled "Corneal Implant Systems and Methods," the contents of which are incorporated entirely herein by reference.

As described above, implants may be formed as xenografts, i.e., tissue that is transplanted between members of different species. For instance, implants for humans may be formed from pig corneas. Studies have shown that the mechanisms of rejection of a corneal xenograft are significantly different from those of a vascularized organ xenograft. Since the cornea is an avascular tissue, hyperacute rejection, which results from vascular occlusion and is typically seen in vascularized solid organ xenografts, has not been evidenced in corneal xenografts. As such, the immune privileged environment of the cornea appears to provide corneal xenografts with some degree of protection from rejection.

Nevertheless, in some cases, the corneal xenografts may be treated to reduce the likelihood of rejection. Studies have shown that corneal xenografts from lyophilized tissue fail to trigger an immune response. During lyophilization, the donor corneal tissue is frozen and water is removed from the donor corneal tissue in the frozen state by a strong vacuum. This process alters structural components of the donor corneal tissue and renders the lyophilized donor corneal tissue less antigenic than fresh donor corneal tissue. It is contemplated that freezing donor corneal tissue reduces its antigenicity by killing cells bearing transplantation antigens.

Other approaches treat the donor corneal tissue to produce acellular corneal xenografts, which reduce the likelihood of rejection. For instance, the donor corneal tissue can be de-cellularized with electron beam or gamma ray processing. High energy electrons or gamma rays can break the chains of DNA to kill cells bearing transplantation antigens.

In further cases, corneal xenografts may be obtained from species that have been genetically-engineered to resist the effects of the host immune response.

Figure 8:
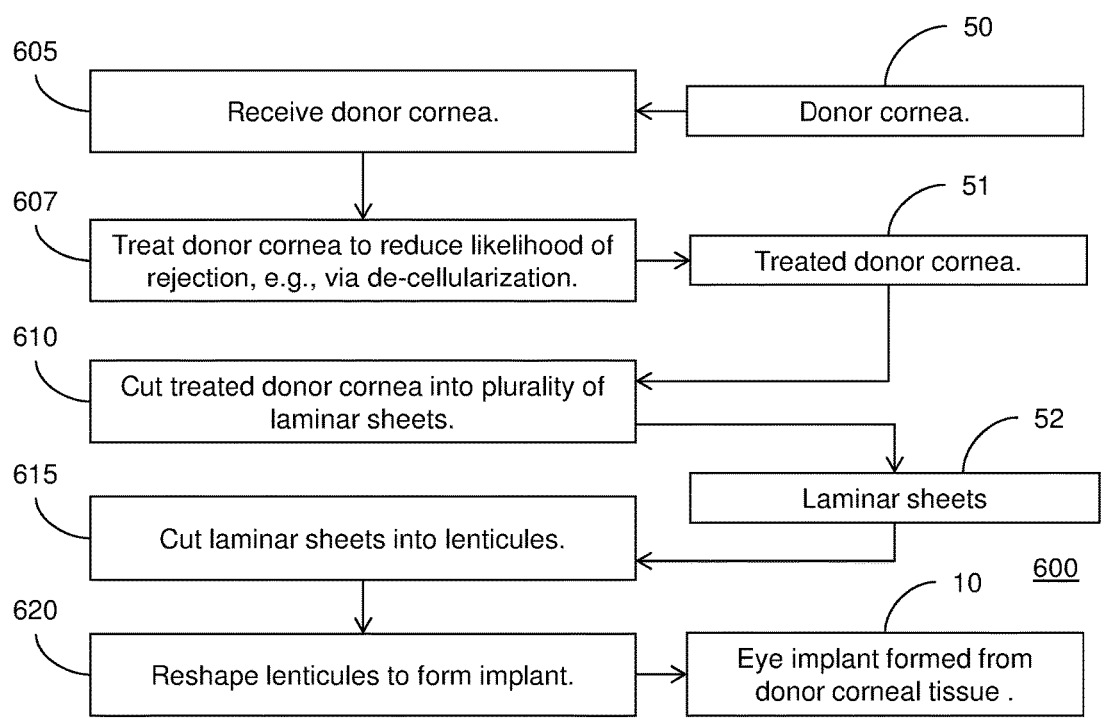
FIG. 8 illustrates an example procedure for processing donor corneal tissue to produce an implant, according to aspects of the present disclosure.

FIG. 8 illustrates an example procedure 600 for processing a donor cornea to manufacture one or more implants 10 as xenografts. In step 605, a donor cornea 50 is received from another species, such as a pig. In step 607, the donor corneal tissue is treated to reduce the likelihood of rejection by the host immune system. For instance, the donor corneal tissue is de-cellularized with electron beam or gamma ray processing, so that cells bearing transplantation antigens are killed.

Figure 9A:
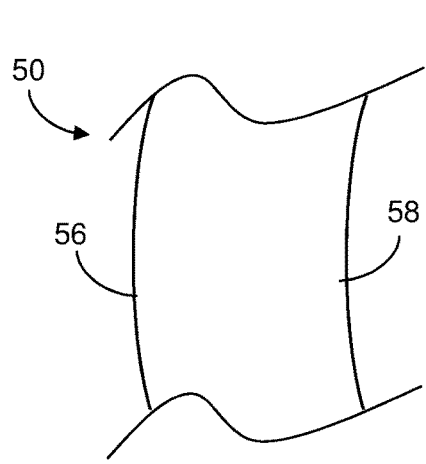
FIG. 9A illustrates a partial sectional view of an example donor cornea, according to aspects of the present disclosure.
Figure 9B:
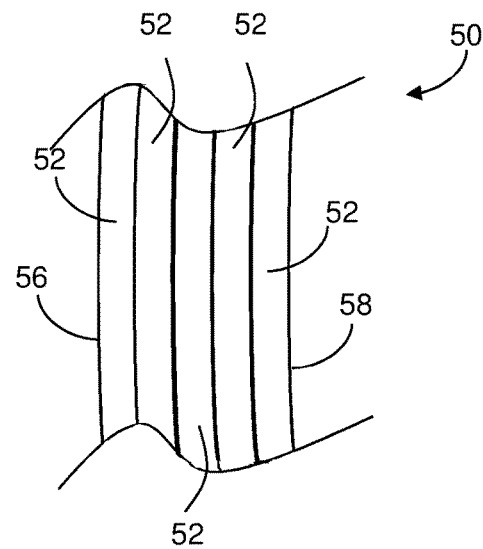
FIG. 9B illustrates the example donor cornea of FIG. 9A cut into laminar sheets, according to aspects of the present disclosure.

In step 610, the treated donor cornea 51 is cut into a plurality of laminar sheets 52. In some embodiments, for example, the laminar sheets 52 may have a thickness of approximately 10 µm to approximately 50 µm; however, it should be understood that the laminar sheets 52 can have other thicknesses. To further illustrate, a partial cross-section of the donor cornea 50 is shown in FIG. 9A prior to the cutting in step 610 and in FIG. 9B after the laminar sheets 52 have been cut from the donor corneal tissue 50 in step 610. As shown in FIGS. 9A-9B, the laminar sheets 52 can be cut such that the thickness of each laminar sheet 52 is measurable in a direction from an anterior surface 56 of the donor cornea 50 to a posterior surface 58 of the donor cornea 58.

Figure 10:
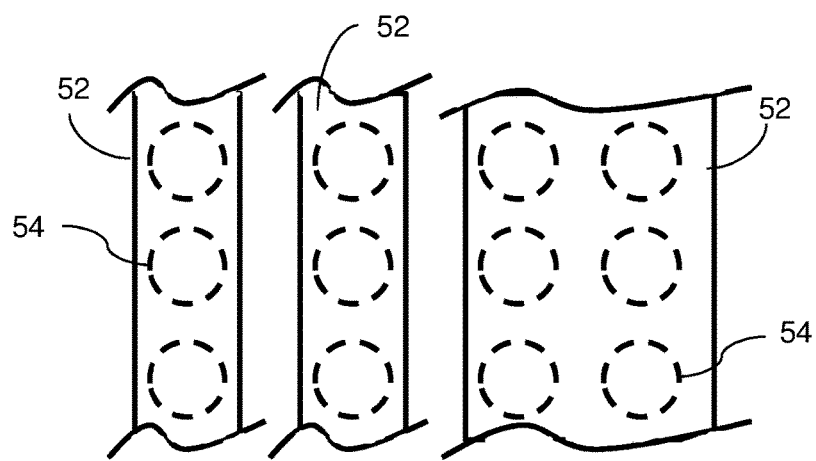
FIG. 10 illustrates an example of a plurality of lenticules to be cut from a plurality of laminar sheets, according to aspects of the present disclosure.

In step 615, one or more lenticules 54 are cut from each of the laminar sheets 50. For example, FIG. 10 shows portions of a plurality of laminar sheets 52 from which one or more lenticules 54 may be cut along the indicated dashed lines. In the illustrated example, the lenticules 54 are each configured to be cut as a disc-shaped piece of corneal tissue 50; however, according to additional and/or alternative aspects of the present disclosure, the one or more lenticules 54 can be cut from the laminar sheet 52 according to other perimeter shapes (e.g., a circular shape, an oval shape, a polygonal shape, a non-polygonal shape, or the like). The process for obtaining the lenticules 54 with the desired shapes may involve precisely measuring the dimensions and/or other characteristics of the donor cornea 51 and/or the laminar sheets 52 to determine how subsequent cutting should proceed.

The dimensions and characteristics of corneal tissue, for instance, can be measured by employing optical coherence tomography (OCT), ultrasound imaging, second-harmonic imaging microscopy, and/or other high resolution measurement technologies. OCT involves low-coherence interferometry using light of relatively long wavelengths (e.g., near-infrared light) to capture micrometer-resolution, three-dimensional images based on the optical scattering by the corneal tissue. Ultrasound imaging involves applying ultrasound pulses to the corneal tissue and generating images based on the varying degrees of reflection of sound by the corneal tissue. Second-harmonic imaging microscopy obtains involves detecting, with a microscope, variations in optical density, path length, refractive index, etc., in the corneal tissue based on variations in the corneal tissue's ability to generate second-harmonic light from incident light.

In step 620, the one or more lenticules 54 are further reshaped for corrective purposes to produce the implants 10. For example, the surfaces of each lenticule 54 can be reshaped (e.g., via cutting and/or ablation) to form an implant 10 having a predetermined size, perimeter shape, thickness, front surface 12 profile, and/or back surface 14 profile to produce the necessary desired correction, e.g., refractive correction. Furthermore, the lenticules 54 may be reshaped to include desired edge characteristics and other features that allow the structure of the implants 10 to blend or transition smoothly into the surrounding eye structure, for instance, to improve optics and/or promote epithelial growth over the implant 10.

In one example implementation, the lenticules 54 can be cut from the laminar sheets 52 in the predetermined size and perimeter shape at step 615 and the implant 10 can be formed by reshaping the front surface 12 and the back surface 14 at step 620. In another example implementation, the lenticules 54 can be cut from the laminar sheets 52 with a first size and/or a first perimeter shape at step 615 and then reshaped at step 620 to have a second size and/or a second perimeter shape, which are different from the first size and first shape, in addition to reshaping the front surface 12 and the back surface 14 at step 620.

The precise cutting and shaping of the implants 10 in the procedure 600 can be achieved, for example, by a femtosecond laser, an excimer laser, and/or other cutting apparatus (e.g., a blade, a clawer, a mechanical keratome, etc.). In one non-limiting example, the laminar sheets 52 are cut from the donor cornea 50 using a femtosecond laser in step 610 and the lenticules 54 are reshaped to form the implants 10 using an excimer laser in step 620. Advantageously, the procedure 600 precisely processes donor corneal tissue to produce a plurality of implants 10 from a single donor cornea 50. The process for reshaping the lenticules 54 to obtain the implants 10 with the desired shapes may involve precisely measuring the dimensions and/or other characteristics of the lenticules 54 to determine how subsequent cutting should proceed. The dimensions and characteristics, for instance, can be measured by employing OCT, ultrasound imaging, second-harmonic imaging microscopy, and/or other high resolution measurement technologies.

Aspects of the procedure 600 can be automated. For example, an automated system can manipulate the lenticules 54 by machine in a "pick and pack" process. Using the laminar sheets 52 facilitates this automated manipulation by the machine.

According to some aspects of the present disclosure, all of the plurality of implants 10 that are produced from a single donor cornea 50 can have the same shape and/or size. However, according to additional and/or alternative aspects of the present disclosure, the plurality of implants 10 can be produced from the single donor cornea 50 in one or more different shapes and/or sizes.

Although the procedure 600 illustrated in FIG. 8 may process the donor cornea 50 from another species to produce implants 10 as xenografts, it is understood that aspects of the procedure 600 may also be applied to human donor cornea to produce implants 10 as allografts.

According to some approaches, a lenticule may be prepared and packaged (e.g., by a supplier) for delivery and subsequent reshaping (e.g., by a practitioner) at or near the time of actual implantation into the cornea. As such, the lenticule may provide a more general shape (e.g., a blank) that can be subsequently reshaped into an implant according to any specific shape. As described above, the specific shape may cause a change in refractive power when implanted. In addition, the shape may include desired edge characteristics and other features that allow the structure of the implant to blend or transition smoothly into the surrounding eye structure, for instance, to improve optics and/or promote epithelial growth over the implant.

Figure 13:
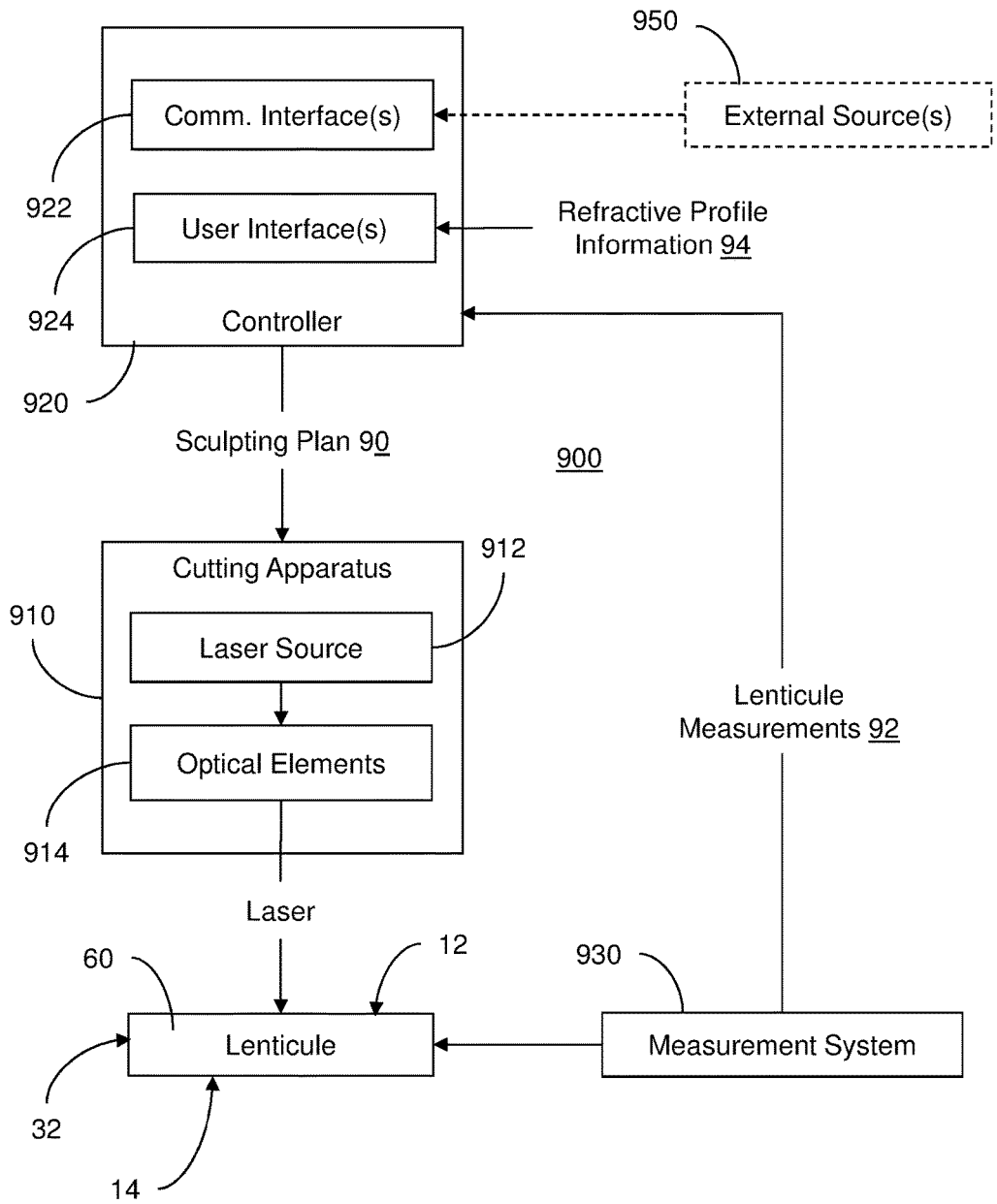
FIG. 13 illustrates yet another example reshaping system for reshaping a lenticule to form an implant, according to aspects of the present disclosure.

If a separate supplier packages and delivers a lenticule as a blank to a practitioner, the practitioner may need to know the starting measurements of the lenticule so that the proper amount of tissue can be accurately removed from the lenticule to obtain a precisely shaped corneal implant. In some approaches, the supplier may take the measurements of the lenticule prior to packaging and may provide the measurements to the practitioner. Additionally, the supplier may provide instructions that the practitioner can follow to reshape the lenticule in order to obtain a particular shape for the implant. For instance, the instructions may indicate what tissue should be removed from particular locations of the lenticule. Such instructions are based on the measurements taken of the lenticule.

Where a lenticule is delivered as a blank to a practitioner, the practitioner may subsequently employ a reshaping system to reshape the lenticule. FIG. 13 illustrates an example reshaping system 900 for reshaping a lenticule 60 formed from donor corneal tissue. For instance, a supplier may produce and package the lenticule 60 on other systems and may deliver the lenticule 60 to a practitioner. The practitioner can then employ the reshaping system 900 to reshape the lenticule 60 and produce an implant 10 with a desired refractive profile to reshape a recipient eye.

As shown in FIG. 13, the reshaping system 900 includes a cutting apparatus 910. The cutting apparatus 910 may include a laser source 912 that emits a laser, such as an excimer laser, capable of cutting corneal tissue. The cutting apparatus 910 may also include one or more optical elements 914 that direct the laser from the laser source. Such optical elements 914 may include any combination of lenses, mirrors, filters, beam splitters, etc.

The reshaping system 900 also includes a controller 920, which may be implemented with at least one processor, at least one data storage device, etc., as described further below. The controller 920 is configured to determine a sculpting plan 90 for modifying a first shape of the lenticule 60 and achieving a second shape for the lenticule 60 to produce the implant 10 with the desired refractive profile. The controller 920 can control the cutting apparatus 910 to direct, via the one or more optical elements 914, the laser from the laser source 912 to sculpt the lenticule 60 according to the sculpting plan 90 to produce the implant 10.

The controller 920 can determine the sculpting plan 90 by processing: (i) measurements 92 relating to the lenticule 60 and (ii) information 94 relating to the refractive profile for the implant 10. The measurements 92 allow the controller 920 to determine the first shape of the lenticule 60. Meanwhile, the information 94 allows the controller 920 to determine the desired refractive profile for the implant 10. As such, the controller 920 can generate the sculpting plan 90 for modifying the lenticule 60 from the first shape indicated by the measurements 92 to a second shape indicated by the information 94.

The measurements 92 may include dimensions and/or other characteristics of the lenticule 60 when the lenticule 60 is initially received by the reshaping system 900. In some embodiments, the reshaping system 900 may include a measurement system 930 communicatively coupled to the controller 900. The measurement system 930 can determine measurements 92 relating to the lenticule 60 and communicate the measurements 92 to the controller 920. The measurement system 930 may employ OCT, ultrasound imaging, second-harmonic imaging microscopy, and/or other high resolution measurement technologies as described above. The controller 920 may control aspects of measurement system 930. As such, the controller 920 can actively control the determination of the measurements 92. The measurement system 930 may also be employed during and/or after the reshaping process to monitor the progress of the sculpting and to assess the resulting implant 10.

Alternatively, the controller 920 may be configured to receive the measurements 92 more passively from one or more external sources 950. For instance, the controller 920 may include one or more communication interfaces 922 for receiving, from the one or more external sources 950, the measurements 92 relating to the lenticule 60. The communication interface(s) 922, for instance, may employ any combination of wired or wireless electronic data communication technologies. Other information, including information 94, may also be communicated between the external source(s) 950 and the controller 920 via the communication interface(s) 922.

The controller 920 may also include one or more user interfaces 924 to receive the information 94 relating to the desired refractive profile for the implant 10. For instance, the practitioner may communicate the information 94 to the controller 920 via an input device, such as a keypad, mouse, remote control, touchpad, touchscreen, etc. In some cases, the information 94 may expressly provide the desired dimensions for the implant 10. In other cases, the information 94 may provide the desired refractive correction and the controller 920 may determine the dimensions for the implant 10 indirectly from the desired refractive correction. For instance, the practitioner may specify the optical power (e.g., in diopters and diameter) needed for the desired refractive correction, and the controller 920 can generate the sculpting plan 90 to produce the implant 10 which achieves the optical power in the recipient eye. Other information, including measurements 92, may also be communicated to the controller 920 via the user interface(s) 924.

Although FIG. 13 shows that the controller 920 receives the measurements 92 relating to the lenticule 60 and the information 94 relating to the refractive profile for the implant 10, it is understood that the controller 920 may also receive and/or determine other types of measurements and/or information to generate the sculpting plan 90. For instance, the controller 920 may receive and/or determine topographic or other measurements relating to the recipient eye. Topographic measurements of the recipient eye may be employed, for instance, to determine the sculpting of the posterior surface of the lenticule 60 so that the recipient eye can better receive the resulting implant 10.

In addition, the controller 920 may take other properties of the lenticule 60 into account. For instance, the sculpting plan 90 generated by the controller 920 may take into account changes in thickness that the implant 10 may experience after it is implanted. If the lenticule 60 is kept in an isotonic solution during sculpting as described further below, the resulting implant 10 may become thinner after it is implanted in the recipient eye. As such, the sculpting plan 90 can anticipate the change in thickness of the implant 10 in vivo and may sculpt the lenticule 60 with a thickness that still achieves the refractive profile after the implant 10 becomes thinner in vivo.

Although the cutting apparatus 910 shown in FIG. 13 may employ a laser, it is understood that the lenticule 60 may be reshaped by applying any appropriate technique with any type of cutting apparatus. In alternative embodiments, for instance, one or more molds may be applied to the lenticule 60 and a blade may be employed to cut the lenticule 60 according to the shape of the mold(s).

In some embodiments, the reshaping system 900 can sculpt any aspect of the lenticule 60 to produce the implant 10. In particular, the cutting apparatus 910 can sculpt the lenticule 60 three-dimensionally along more than one surface of the lenticule 60, e.g., the anterior and posterior surfaces, to produce the implant 10. FIG. 13 illustrates the surfaces of the lenticule 60 corresponding to the front surface 12, the back surface 14, and the peripheral edge 32 of the implant 10. As described above, the front surface 12 corresponds to the anterior of the eye when the implant 10 is implanted and the back surface 14 corresponds to the posterior of the eye when the implant 10 implanted. The laser can be guided to any portion of the lenticule 60 with the optical elements 914 and, optionally, other mechanical or electromechanical mechanism(s) (not shown) that move the cutting apparatus 910 relative to the lenticule 60.

The measurements 92 relating to the lenticule 60 may include three-dimensional measurements for the lenticule 60 specifying thickness, shape, and/or dimensions for multiple surfaces, etc. Such three-dimensional measurements can be obtained, for instance, via OCT, ultrasound imaging, second-harmonic imaging microscopy, and/or other high resolution measurement technologies as described above. Correspondingly, the controller 920 can generate a three-dimensional sculpting plan 90 that instructs the cutting apparatus 910 to sculpt the lenticule 60 three-dimensionally to achieve the refractive profile based on the information 94. In contrast, other approaches only receive surface topography measurements and are limited to sculpting the anterior surface of the lenticule 60. Advantageously, to generate the three-dimensional sculpting plan 90, the controller 920 can precisely and accurately determine the three-dimensional distribution of the volume added by the implant 10 in the recipient eye.

The implant 10 has a thickness, one or more radius of curvature, and other three-dimensional characteristics that determine the volume it adds to the cornea. Controlling the three-dimensional distribution of the added volume allows the desired refractive correction to be achieved more precisely and accurately. In general, the reshaping system 900 may be employed to provide volume-based reshaping of the recipient eye. To facilitate implantation of the three-dimensionally shaped implant 10, the controller 920 may control the cutting apparatus 910 or other device to mark the implant 10, e.g., on the front surface 12 and/or the back surface 14, to indicate the proper orientation for implantation.

Furthermore, as described above, lenticules may be delivered as blanks to a practitioner from a supplier, and the practitioner may subsequently employ the reshaping system 900 to reshape the lenticules for custom implants. Although the lenticules are formed as blanks, differences between the sources of donor corneal tissue and/or between suppliers of the lenticules may produce lenticules with variations in thickness and other characteristics. As such, the three-dimensional measurements 92 of the lenticule 60 provide a precise and accurate baseline for the reshaping process to achieve the desired refractive correction.

Figure 11:
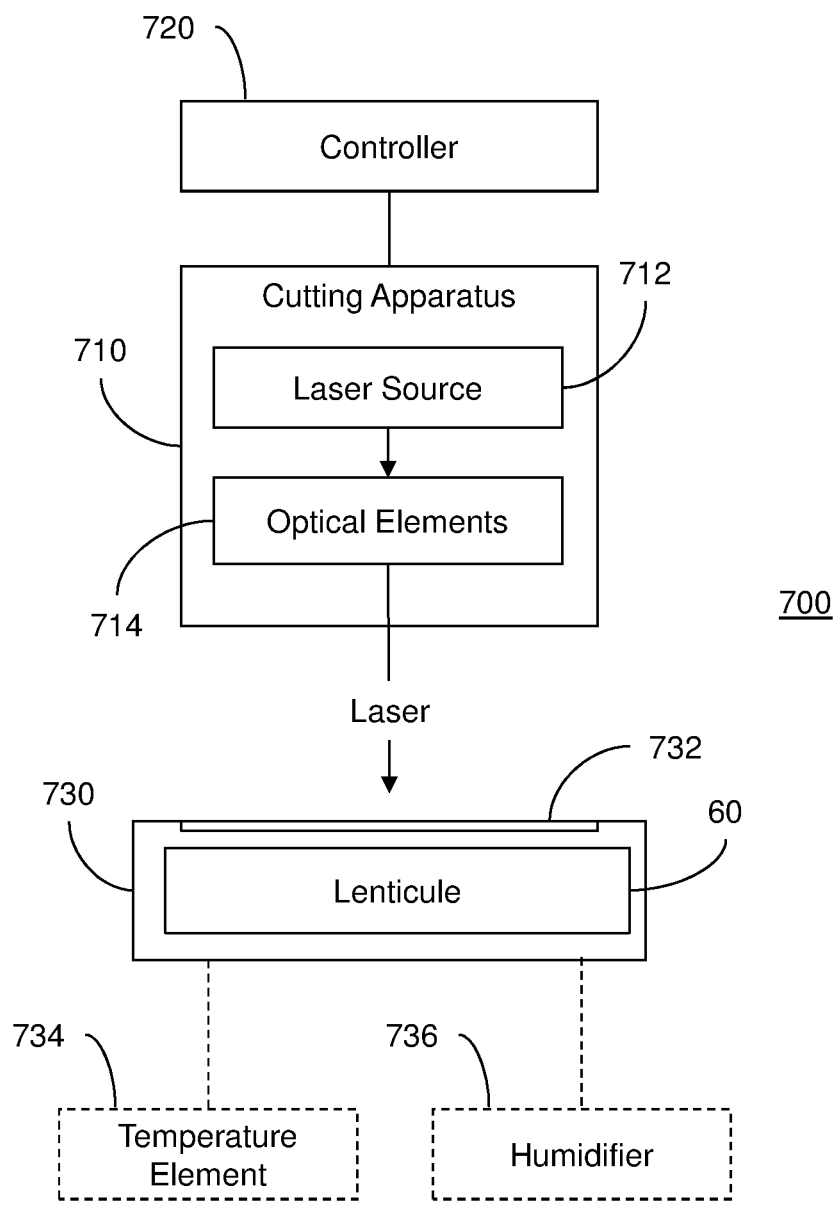
FIG. 11 illustrates an example reshaping system for reshaping a lenticule to form an implant, according to aspects of the present disclosure.

FIG. 11 illustrates another example reshaping system 700 that allows a lenticule 60 to be reshaped in a controlled environment. As shown in FIG. 11, the reshaping system 700 includes a cutting apparatus 710 for reshaping a lenticule 60 and an enclosure 730 with an interior for receiving and holding the lenticule 60. The enclosure 730 may be sealed and can help to control the state of the lenticule 60 disposed in the interior. The state of the lenticule 60 may include hydration, temperature, etc. In addition, the enclosure 730 can maintain the sterility of the lenticule 60 and/or minimize exposure to ultraviolet light.

The cutting apparatus 710 may include a laser source 712 that emits a laser, such as an excimer laser, capable of cutting corneal tissue. The cutting apparatus 710 may also include one or more optical elements 714 that direct the laser from the laser source. Such optical elements 714 may include any combination of lenses, mirrors, filters, beam splitters, etc. Aspects of the cutting apparatus 710 may also be controlled by a controller 720.

The cutting apparatus 710 may reshape the lenticule 60 with the laser while the lenticule 60 is disposed in the enclosure 730. Accordingly, the enclosure 730 includes a closed window 732 that allows the laser to pass into the enclosure 730 and cut the lenticule 60. The closed window 732 may be formed from any suitable translucent material, such as a plastic or glass.

In alternative embodiments, rather than employing a closed window 732, the enclosure 730 may have an opening that allows the laser to pass into the enclosure 730. A positive pressure may be employed in the enclosure 730 to maintain the desired conditions in the enclosure 730.

For the embodiments above, the enclosure 730 may be configured to accommodate mechanisms for actively maintaining temperature, humidity, and/or positive pressure in the enclosure 730. For instance, the enclosure 730 may accommodate a temperature (e.g., heating) element 734 and/or a humidifier 736.

Figure 12:
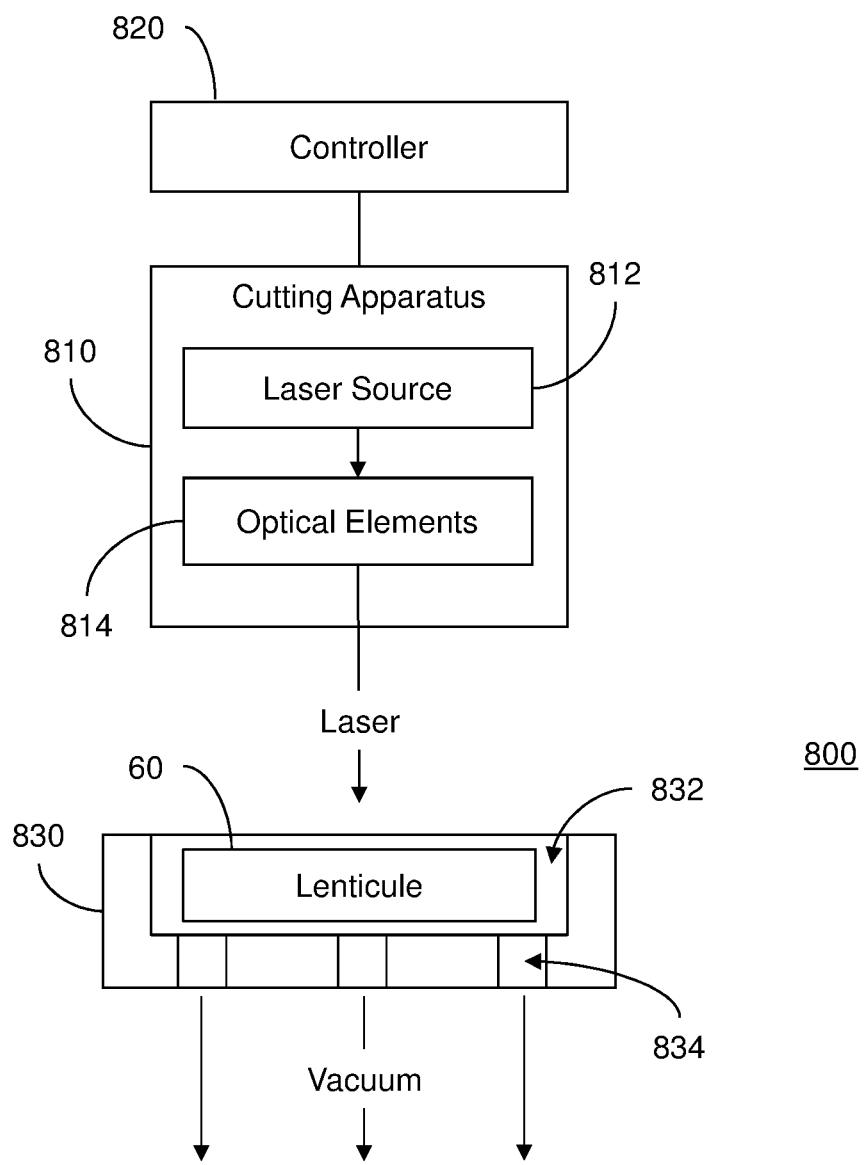
FIG. 12 illustrates another example reshaping system for reshaping a lenticule to form an implant, according to aspects of the present disclosure.

FIG. 12 illustrates yet another reshaping system 800 that also allows a lenticule to be reshaped. As shown in FIG. 12, the reshaping system 800 includes a cutting apparatus 810. The cutting apparatus 810 may include a laser source 812 that emits a laser, such as an excimer laser, capable of cutting corneal tissue. The cutting apparatus 810 may also include one or more optical elements 814 that direct the laser from the laser source. Such optical elements 814 may include any combination of lenses, mirrors, filters, beam splitters, etc. Aspects of the cutting apparatus 810 may be controlled by a controller 820.

The reshaping system 800 also includes a stage 830 for holding the lenticule 60. The stage 820 includes a recess 832 that is configured to receive the lenticule 60. The cutting apparatus 810 may reshape the lenticule 60 with the laser while the lenticule 60 is disposed in the recess 832. When the lenticule 60 is placed in the recess 832, the recess 832 may be filled with a hydrating fluid, e.g., balanced salt solution (BSS) or other standardized salt solution, to maintain the lenticule 60 in a hydrated state. The recess 832 includes one or more evacuation mechanisms for drawing the hydrating fluid from the recess 832. For instance, the recess 832 may include vacuum apertures 834. When the cutting process is set to begin, a vacuum may be applied to the vacuum apertures 834 to remove the hydrating fluid from the recess 834 and allow the laser to cut the lenticule 60. The cutting process is sufficiently short in duration to allow the lenticule 60 to remain hydrated during the reshaping process even in the absence of the hydrating fluid.

The hydrating fluid may also maintain an isotonic state for the lenticule 60. In vivo, the cornea does not maintain an isotonic thickness, as the corneal endothelial pumps are continually working to dehydrate the cornea slightly. As such, the thickness of the corneal tissue in vivo may be a slightly smaller than what its thickness would be in an isotonic solution. Therefore, when cutting the lenticule 60, the reshaping system 800 may take into account that the implant 10 sculpted from the lenticule 60 may become thinner after it is implanted in the recipient eye.

In general, the reshaping systems 700 and 800 provide examples of a system for forming a corneal implant, where a receptacle (e.g., enclosure 730, stage 830/recess 832, etc.) receives a lenticule and maintains a state (e.g., hydration, temperature, etc.) of the lenticule. The receptacle may be designed for cost and may be configured to be disposable. As with the reshaping system 900, the lenticule 60 may be delivered as a blank to a practitioner from a supplier, and the practitioner may subsequently employ the reshaping system 700, 800 to reshape the lenticule 60 to produce an implant 10. Indeed, some embodiments may combine aspects of any of the reshaping systems 700, 800, 900. The receptacle provides a controlled environment for precise and predictable cutting by a cutting apparatus. For instance, the per-pulse cutting rate for a laser may be sensitive to hydration of the lenticule 60, so the lenticule 60 may need to be predictably hydrated for precise and accurate sculpting.

Figure 14:
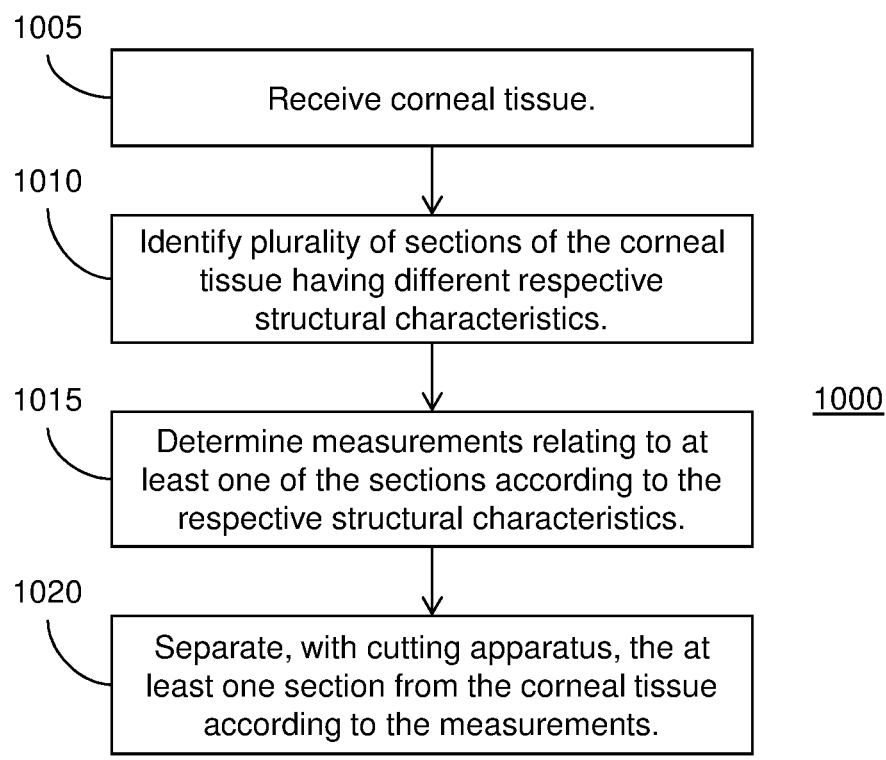
FIG. 14 illustrates another example procedure for processing donor corneal tissue to produce an implant, according to aspects of the present disclosure.

FIG. 14 illustrates an example method 1000 for forming a corneal implant. In step 1005, the method 1000 receives corneal tissue. In step 1010, the method identifies a plurality of sections of the corneal tissue having different respective structural characteristics. In step 1015, the method 1000 determines measurements relating to at least one of the sections according to the respective structural characteristics. In step 1020, the method 1000 separates, with a cutting apparatus, the at least one section from the corneal tissue according to the measurements.

Sections of corneal tissue at different depths may have different respective structural characteristics, so a section of corneal tissue having desired structural characteristics may be obtained from a given depth in the corneal tissue. Thus, according to one embodiment of the method 1000, the plurality of sections may be identified according to a respective depth of each section in the corneal tissue, and the measurements are determined according to the respective depth of the at least one section.

According to another embodiment, the method further includes packaging the at least one section for subsequent implant into a recipient eye.

According to yet another embodiment, the at least one section includes an anterior section of the corneal tissue including the Bowman's membrane. Advantageously, the presence of the Bowman's membrane for an onlay implant enhances epithelial attachment and growth over the onlay implant.

As described above, according to some aspects of the present disclosure, some or all of the steps of the above-described and illustrated procedures can be automated or guided under the control of a controller (e.g., the controller 520, 620, 720, 820). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. More-over, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

I claim:

1. A system for forming a corneal implant, comprising:
a cutting apparatus including:
 a laser source that emits a laser; and
 one or more optical elements that direct the laser from the laser source;
a controller implemented with at least one processor and at least one data storage device, the controller configured to:
 generate a sculpting plan for modifying a first shape of a lenticule formed from corneal tissue and achieving a second shape for the lenticule to produce a corneal implant with a refractive profile to reshape a recipient eye, the sculpting plan determined from:
  measurements relating to the lenticule having the first shape, and
  information relating to a refractive profile for a corneal implant, and
 control the cutting apparatus to direct, via the one or more optical elements, the laser from the laser source to sculpt the lenticule according to the sculpting plan to produce the corneal implant with the refractive profile; and
a receptacle for sculpting the lenticule according to the sculpting plan, the receptacle including an enclosure having an interior configured to receive the lenticule and to maintain at least one of a hydration state or a temperature of the lenticule.

2. The system of claim 1, wherein the measurements relating to the lenticule include three-dimensional measurements of the lenticule, and the cutting apparatus sculpts the lenticule along more than one surface of the lenticule according to the sculpting plan.

3. The system of claim 1, wherein the information relating to the refractive profile includes optical power for the refractive profile to reshape the recipient eye, and the controller determines the sculpting plan to sculpt the lenticule to produce the corneal implant to achieve the optical power in the recipient eye.

4. The system of claim 1, wherein the cutting apparatus is configured to sculpt the lenticule according to the sculpting plan by reshaping an anterior surface and a posterior surface of the lenticule to achieve the refractive profile, the anterior surface corresponding to an anterior of the recipient eye and the posterior surface corresponding to a posterior of the recipient eye.

5. The system of claim 1, wherein the controller is further configured to determine the measurements relating to the lenticule.

6. The system of claim 1, wherein the controller is further configured to receive, from one or more external sources, the measurements relating to the lenticule.

7. The system of claim 1, further comprising a measurement system communicatively coupled to the controller, the measurement system determining the measurements relating to the lenticule and communicating the measurements to the controller.

8. The system of claim 7, wherein the measurement system includes at least one of an optical coherence tomography system, an ultrasound imaging system, or second-harmonic imaging system.

9. The system of claim 1, wherein the controller includes:
one or more communication interfaces for receiving, from one or more external sources, the measurements relating to the lenticule; and
one or more user interfaces for receiving the information relating to the refractive profile for the corneal implant.

10. The system of claim 1, wherein the enclosure is sealable to maintain at least one of the hydration state or the temperature of the lenticule in the interior, the receptacle including a closed window that allows the laser to pass therethrough into the interior of the enclosure.

11. The system of claim 1, wherein the enclosure includes an open window that allows the laser to pass into the interior of the enclosure.

12. The system of claim 1, wherein the receptacle includes:
a recess configured to receive the lenticule and fluid; and
one or more evacuation mechanisms for drawing the fluid from the recess, and
in response to the drawing of the fluid from the recess, the controller is configured to control the cutting apparatus to cut the lenticule according to the sculpting plan.

13. The system of claim 12, wherein the one or more evacuation mechanisms include one or more apertures disposed in the recess and coupled to a vacuum source, and the vacuum source is operable to draw the hydrating fluid from the recess via the one or more apertures.

14. The system of claim 1, wherein the sculpting plan is further determined according to a change in the hydration state of the lenticule.

15. The system of claim 1, wherein the enclosure is configured to maintain a sterility of the lenticule.

16. The system of claim 1, wherein the enclosure is configured to block the lenticule from exposure to ultraviolet light.

* * * * *